(12) United States Patent
Gijtenbeek et al.

(10) Patent No.: US 11,051,508 B2
(45) Date of Patent: Jul. 6, 2021

(54) APPARATUS AND METHOD FOR PRESERVING MUCOSA

(71) Applicant: Merck Sharp & Dohme Corp., Rahway, NJ (US)

(72) Inventors: Adolph Bartholomeus Gijtenbeek, Oss (NL); Harry van Tuijn, Oss (NL); Marinus Johannes Gerardus Maria Ploegmakers, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 124 days.

(21) Appl. No.: 16/381,348

(22) Filed: Apr. 11, 2019

(65) Prior Publication Data

US 2019/0230917 A1 Aug. 1, 2019

Related U.S. Application Data (62) Division of application No. 15/053,736, filed on Feb. 25, 2016, now abandoned, which is a division of application No. 14/093,948, filed on Dec. 2, 2013, now abandoned, which is a division of application
(Continued)

(51) Int. Cl.
| | |
|---|---|
| *A22B 7/00* | (2006.01) |
| *A01N 1/00* | (2006.01) |
| *B01F 15/00* | (2006.01) |
| *B01F 3/12* | (2006.01) |
| *A01N 1/02* | (2006.01) |
| *B01F 15/02* | (2006.01) |
| *A61L 2/18* | (2006.01) |
| *B01F 7/18* | (2006.01) |
| *B01F 13/04* | (2006.01) |

(Continued)

(52) U.S. Cl.
CPC .............. *A01N 1/00* (2013.01); *A01N 1/02* (2013.01); *A22B 7/008* (2013.01); *A61L 2/18* (2013.01); *B01F 3/1221* (2013.01); *B01F 7/18* (2013.01); *B01F 13/047* (2013.01); *B01F 13/10* (2013.01); *B01F 15/00155* (2013.01); *B01F 15/00779* (2013.01); *B01F 15/0283* (2013.01); *C08B 37/0075* (2013.01); *A01N 1/0231* (2013.01); *B01F 2013/1091* (2013.01)

(58) Field of Classification Search
None
See application file for complete search history.

(56) References Cited

U.S. PATENT DOCUMENTS

| | | |
|---|---|---|
| 4,120,656 A | 10/1978 | Henningsen |
| 4,362,033 A | 12/1982 | Yong |

(Continued)

*Primary Examiner* — Neil N Turk
(74) *Attorney, Agent, or Firm* — Yingying Zeng; John C. Todaro (57) ABSTRACT

A mixing apparatus (1) for mixing slaughter offal with a preservative agent, the apparatus comprising an offal collection tank (3) with a bottom (4) provided with a discharge opening (5) connectable to a closable discharge, an agitator (8) extending into the offal collection tank, and a pump unit (9) operatively connectable to the discharge, wherein the apparatus further comprises a preservative reservoir (7) mounted on top of the collection tank (3). A collection and preservation system is provided, wherein the addition of preservation agent can be strictly controlled, can easily and quickly be installed and connected when it is to be used. After use, the system is easily removed and cleaned.

2 Claims, 8 Drawing Sheets

Related U.S. Application Data

No. 12/841,864, filed on Jul. 22, 2010, now abandoned.

(60) Provisional application No. 61/227,984, filed on Jul. 23, 2009.

(51) Int. Cl.
*B01F 13/10* (2006.01)
*C08B 37/00* (2006.01)

(56) References Cited

U.S. PATENT DOCUMENTS

| | | |
|---|---|---|
| 2005/0237852 A1 | 10/2005 | Chandran |
| 2007/0137492 A1 | 6/2007 | Stamper et al. |

APPARATUS AND METHOD FOR PRESERVING MUCOSA

This application is a divisional of U.S. patent application Ser. No. 15/053,736, filed Feb. 25, 2016; which is a divisional of U.S. patent application Ser. No. 14/093,948, filed Dec. 2, 2013; which is a divisional of U.S. patent application Ser. No. 12/841,864, filed on Jul. 22, 2010; which claims the benefit of U.S. Provisional Patent Application No. 61/227,984, filed on Jul. 23, 2009; all of which are herein incorporated by reference in their entireties.

The present invention relates to a mixing apparatus, particularly for mixing slaughter offal, such as porcine intestinal mucosa, with a preservative agent to prepare it for further processing, such as the extraction of pharmaceutically active ingredients, such as heparin.

Heparin is used as an anticoagulant and antithrombotic agent in the treatment and prevention of venous thrombosis. It is generally obtained by isolation from animal tissues. A typical source of heparin is porcine intestinal mucosa, which can be collected at slaughter houses. The mucosa can be removed from the intestines and collected in pure form, from hacked ribbons or from total hash gut, i.e. finely minced intestines resulting in a mucosa containing paste.

When the mucosa is collected, a preservative agent has to be added to prevent decay. Usually, sodium metabisulfite is used as a preservative agent, e.g., in amounts of 0.5-5 kg per 100 liters of mucosa. Alternative preservatives, such as calcium propionate or phenol or any suitable mixtures thereof, can also be used.

The concentration of preservative agent in the collected mucosa has to be strictly controlled. When the concentration of preservative agent is too low the mucosa will decay resulting in the formation of $H_2S$. Exposure to high levels of $H_2S$, such as 500 ppm or more, can result in unconsciousness within seconds and death by loss of breathing. Exposure to lower levels of $H_2S$, even as low as 25 ppm, may cause eye complaints, a sore throat and cough, nausea, shortness of breath, and fluid in the lungs. Many personal safety gas detectors, such as those used by utility, sewage and petrochemical workers, are set to alarm at as low as 5 to 10 ppm and to go into high alarm at 15 ppm.

When the concentration of preservative agent is too high it might interfere with the extraction of heparin from the mucosa later on using an ion exchange resin.

Furthermore, mucosa is normally collected in a small collection tank during the day. When the small collection tank is full, the content is transferred to a large storage reservoir. When the storage reservoir is full after a couple of days the contents are transferred to a tanker lorry for transport of the mucosa to the heparin factory. Any mishap in adding the preservative agent to the small collection tank during the day may result in the decay of the mucosa not only in the small collection tank but also of all mucosa present in the large storage reservoir.

Accordingly, it is of importance that as soon as the mucosa is collected in the slaughter house, the preservative agent is added in a controlled manner so to ensure that the concentration of preservative agent is high enough in the mucosa.

U.S. Pat. No. 4,120,656 discloses an apparatus for collecting and stabilizing intestinal mucosa with an automated metering control for metering the preservative agent into a mucosa collection tank. The metering of the preservative agent starts when the mucosa reaches a bottom liquid level, the level of mucosa rising, whereby an impulse from a time clock started by a control unit determines the pumping time.

First of all, mucosa is added to the collection tank without any preservative agent present. Furthermore, any mishap in metering the preservative agent from the preservative reservoir to the collection tank results in the concentration of the preservative agent to be too low, resulting in the above-mentioned formation of $H_2S$. Finally, such collection tanks typically comprise a relative large number of parts and connections which makes it difficult to properly install the system or to dismantle it, e.g., for cleaning purposes after use.

It is an object of the invention to provide a collection and preservation system, wherein the addition of preservation agent can be strictly controlled, that can easily and quickly be installed and connected when it is to be used. After use, the system should be easily removed and cleaned.

The object of the invention is achieved with a mixing apparatus for mixing slaughter offal with a preservative agent, the apparatus comprising an offal collection tank with a bottom provided with a discharge opening connectable to a closable discharge, an agitator extending into the offal collection tank, and a pump unit operatively connectable to the discharge, wherein the apparatus further comprises a preservative reservoir mounted on top of the collection tank.

The collection tank can be provided with one or more supports for carrying the preservative reservoir. Such a support for the preservative reservoir can be detachable. The collection tank may comprise a connection point for the support at two opposite sides of the agitator, so the user has the freedom to choose where he wants to attach the reservoir. Optionally, the preservative reservoir is adjustable in height.

The collection tank can be provided with a sensor to determine when the collected mucosa compound reaches a certain maximum level. A programmable control unit can be used to stop the supply of mucosa compound to the collection tank after the sensor detects that the maximum level is reached. Before or during collection, the required amount of preservative agent is added and the agitator is activated to stir and homogenize the mixture. Optionally, about 10 vol % additional preservative agent is added to ensure that all of the mucosa is effectively preserved. After the sensor detects that the maximum level is reached and the supply of mucosa is stopped, the supply of preservative agent can also be stopped. After stopping the supply of mucosa the stirring by the agitator may be continued, e.g., for six minutes or more, preferably for at least ten minutes. Subsequently, the control unit opens the discharge and activates the pump unit and preserved mucosa compound is discharged to a container or storage tank. When the level of the preserved mucosa in the collection tank reaches a certain minimum level, the control unit closes off the discharge and deactivates the pump unit. The control unit restarts the supply of mucosa compound and preservative agent until the maximum level is reached again. It is required that the supply of preservative agent starts at least together with the supply of the mucosa.

It is preferred that the addition of preservative agent starts before the collection of mucosa is started. More preferably, before the collection of mucosa is started, the total of the required amount of preservative agent is added. After the sensor detects that the maximum level of mucosa is reached, the supply of mucosa is stopped and the preserved mucosa is discharged. Optionally, a second sensor in the collection tank can be present to detect the minimum level of mucosa. Alternatively, the discharge pump is operated for a calculated amount of time to ensure that the mucosa level in the collection tank has reached the minimum level.

By maintaining a minimum level of preserved mucosa compound in the collection tank during the complete process cycle, it is prevented that isolated portions of mucosa, e.g., in the discharge line, are insufficiently mixed with the preservative agent.

During or after discharge of the preserved mucosa compound, the preservative reservoir can be refilled, e.g., by a user or automatically. The preservative reservoir can be dimensioned in such a way that its content corresponds to the volume of preservative agent needed to preserve the mucosa volume between the maximum and minimum levels in the collection tank.

More preferably, the preservative reservoir is provided with two sensors to detect a minimum and a maximum level.

In a preferred embodiment, operation starts with an empty preservative reservoir and an empty collection tank. The minimum level in the preservative reservoir detects the absence of preservative agent and starts filling the preservative reservoir. When the first sensor detects the maximum level in the preservative reservoir, the control unit stops the supply of preservative agent and the total amount of preservative agent is added to the collection tank. When the second sensor detects the minimum level reached in the preservative reservoir, the control unit starts the supply of mucosa. After the sensor detects that the maximum level is reached the supply of mucosa is stopped. Subsequently, the control unit opens the discharge and activates the pump unit and preserved mucosa compound is discharged to a container or storage tank. When the level of the preserved mucosa in the collection tank reaches a certain minimum level, the control unit closes off the discharge and deactivates the pump unit. Then the cycle is started again with the filling of the preservative reservoir.

It has been found that the use of liquid preservatives, in particular an aqueous solution of a metabisulfite, such as sodium metabisulfite, allows more accurate metering and dosing. A suitable aqueous solution is for instance a solution of 30-45 vol. % of sodium metabisulfite.

Using the programmable control unit and automated dosing and metering cycles, the preservative agent can be metered very accurately. Variations and deviations of preservative content in the discharged preserved mucosa can substantially be reduced.

In a specific embodiment of the apparatus according to the present invention, the collection tank may comprise a second discharge opening at a lower level than the first discharge opening. The lower second discharge opening can be used for completely emptying the collection tank, e.g., for cleaning purposes. The higher first discharge opening can be used to discharge the mucosa compound after mixing the preservative agent into it to a collection tank. To ensure that also the mucosa below the higher first discharge opening is effectively stirred, the agitator has a lowest end between the level of the first discharge opening and the level of the second discharge opening. The bottom of the collection tank may taper down to the lower second discharge opening, e.g., under an angle of about 5-30 degrees, e.g., about 20 degrees.

The lower second discharge opening may be connected to a hose tube, e.g., with a shut-off valve. Optionally, the hose tube can be supported by a rotatable support allowing selective positioning of the hose tube end. The rotatable support can for example comprise a piping clip on a rotatable arm, e.g., having its axis of rotation in line with the second discharge opening.

The agitator can be positioned in such a way that it has its longitudinal axis under an angle with the vertical. The angle can for example be between 5-30 degrees, e.g., about 20 degrees. This enables to position its lower end near the centre line of the collection tank, while the drive unit is positioned near the periphery of the collection tank and easily accessible for a user.

A lid can be used to close off the collection tank. The lid can for example have a permanently closed lid section and a removable lid section. Optionally, the removable lid section is linked to the permanently closed lid section by means of one or more hinges. The permanently closed section can be provided with filling orifices for filling the collection tank with the mucosa compound and/or for adding the preservative agent. The agitator can be fixed to the closed lid section, e.g., in the middle of it, with its stirrer rod extending into the collection tank and its drive unit placed on top of the permanently closed lid section. To enhance options for use and for positioning the apparatus, filling orifices can be provided at both sides of the drive unit of the agitator. In addition, the sensor for detecting the maximum level of mucosa compound in the collection tank can also be positioned at both sides of the drive unit of the agitator. In an alternative embodiment, the filling orifice for the mucosa compound is positioned at one side of the drive unit of the agitator and the sensor for detecting the maximum level of mucosa compound in the collection tank is positioned at the other side of the drive unit of the agitator so to ensure that the maximum level sensor is not sprayed with mucosa compound before the maximum level of mucosa compound in the tank is reached and the supply of mucosa compound is stopped too early.

For a better closure of the collection tank, the removable lid section can be provided with a folded edge covering the upper edge of the collection tank when the lid section is in the closed position. Furthermore, the adjacent edges of the hingeable lid section and the permanently closed lid section can be provided with raised edges. The raised edge of the hingeable lid section can be folded over the raised edge of the permanently closed section and connected to the one or more hinges.

For safety reasons, the collection tank may comprise a sensor arranged to send a stop signal to a control unit for the agitator when the hingeable lid section is not in its closed position.

The apparatus may further comprise a support pallet carrying the collection tank. This way, a mobile unit is obtained which can easily be installed or removed and which can be made very compact allowing a modular set-up.

The support pallet can for example comprise positioners for positioning the pump unit. The positioners can for example be raised edges fitting around the periphery of the pump unit base or around its support feet. This way, the pump unit can be easily positioned and removed, respectively. It can be positioned close to the collection tank to minimize the length of the hose pipe or tube connecting it to the discharge of the collection tank. Rapid-action couplings can be used to couple the pump unit to the collection tank discharge.

The support pallet can for example be a frame, e.g., of a corrosion resistant metal, such as corrosion resistant steel. The frame can for instance be a rectangular frame with one or more cross beams that may be parallel and/or under right angles with each other, balancing requirements of light weight and mechanical strength.

To reduce risks of damages, the dimensions of the pallet can be made such that, in plan view, none of the other components of the apparatus extends past the outline of the pallet.

The collection tank can for example rest on three or more legs fixed to the frame. The frame itself can be provided with height adjustable supports.

Optionally, the collection tank may be provided with a guiding bar for attachment of electric cables. The guiding bar can for example extend horizontally over part of the outer wall of the collection tank.

The mucosa containing compounds to be processed are generally pasty and may often comprise minced intestinal tissue. These features demand the use of highly reliable and robust pump types. Diaphragm pumps are a particularly suitable type of pump unit. Other types of pump units can also be used if so desired.

The automatic dosing and metering of the preservative agent and the use of fixed minimum and maximum preservative levels and a fixed maximum mucosa level result in a very reliable and accurate preservation system with only small deviations in preservative content in the mixed product.

The compact and modular set-up and the various possibilities of height adjustment and the users freedom to select righthand or lefthand placement of the preservative reservoir and/or the connection to the mucosa supply, result in a very versatile design of the apparatus, which therefore can easily and quickly be installed and connected in any part of the slaughter house, easily be removed and cleaned, and is very ergonomical.

The present invention will be elucidated with reference to the figures wherein.

Figure 1:
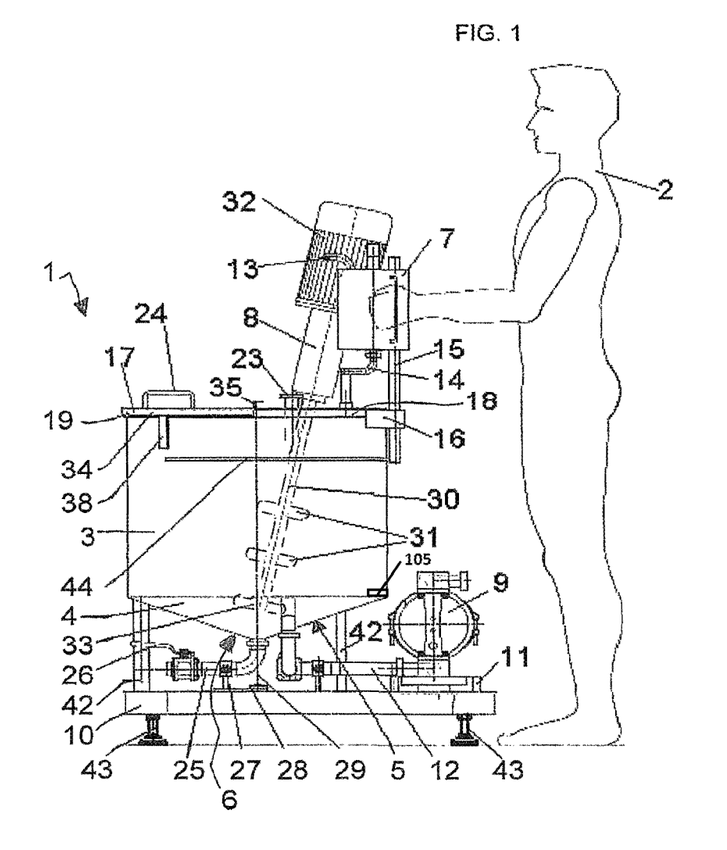
FIG. 1: shows a side view of an apparatus according to the present invention.

FIG. 1 shows a mixing apparatus 1 for mixing porcine intestinal mucosa with a preservative agent and a user 2 standing next to it. The mixing apparatus 1 comprises an offal collection tank 3 with a bottom 4 provided with a higher first discharge opening 5, a lower second discharge opening 6, a preservative reservoir 7, an agitator 8 extending into the offal collection tank 3, a diaphragm pump 9 and a support pallet 10 carrying the collection tank 3. The lower second discharge opening 6 can be used for completely emptying the collection tank, e.g., for cleaning purposes. The higher first discharge opening 5 is used to discharge the mucosa compound after mixing the preservative agent into it to a storage tank.

Figure 3:
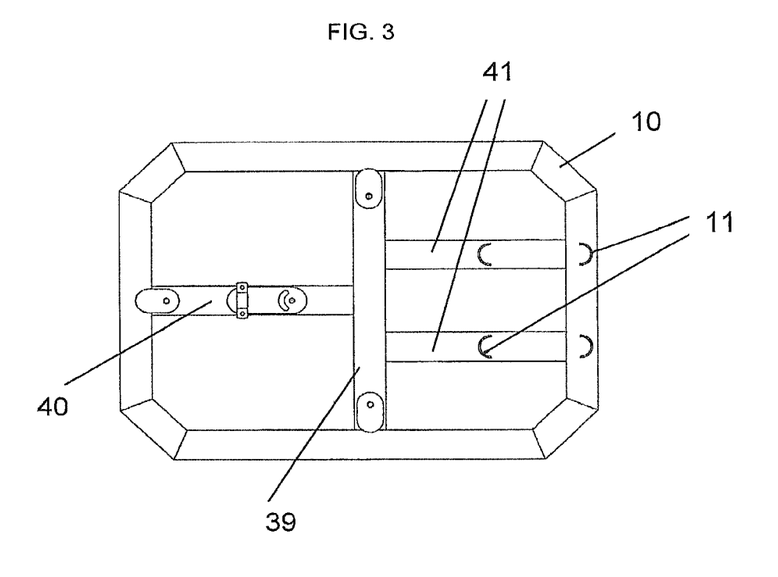
FIG. 3: shows the pallet of the apparatus of FIG. 1 in plan view.

The support pallet 10, shown separately in FIG. 3, comprises upstanding positioners 11 for positioning the diaphragm pump 9. The positioners 11 fit around a part of the periphery of the pump base in such a way that the position of the pump 9 in the horizontal plane is fixed. A discharge line 12 leads from the first discharge opening 5 in the collection tank 3 to the pump 9. The pump 9 has an outlet connected to a line leading to a storage tank (not shown), where the preserved mucosa is stored for further processing.

The preservative reservoir 7 is a cylindrical reservoir with a supply connection 13 on top and a discharge connection 14 at its bottom. The preservative reservoir 7 is attached to a vertical support bar 15 which is adjustable in height via a guiding opening in a support arm 16 projecting horizontally from the collection tank 3. The collection tank 3 is provided with two of such support arms 16: one at both sides of the agitator 8, so the user has the freedom to choose whether he prefers to position the preservative reservoir 7 left or right from the agitator 8. The preservative reservoir 7 comprises two inlets 45 for a maximum level sensor and a minimum level sensor. Furthermore, the preservative reservoir comprises a vent 46.

Figure 5:
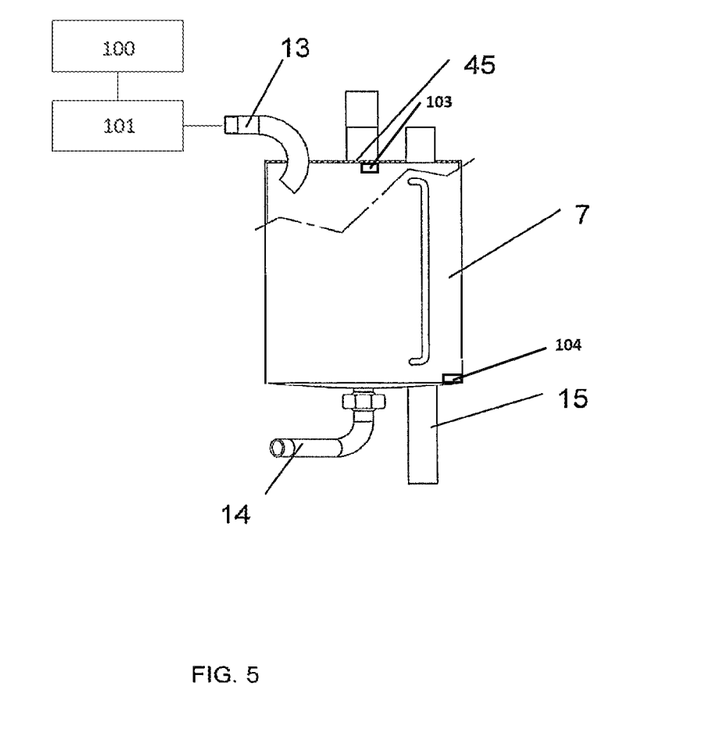
FIG. 5: shows a cross section of the preservative reservoir 7.
Figure 6:
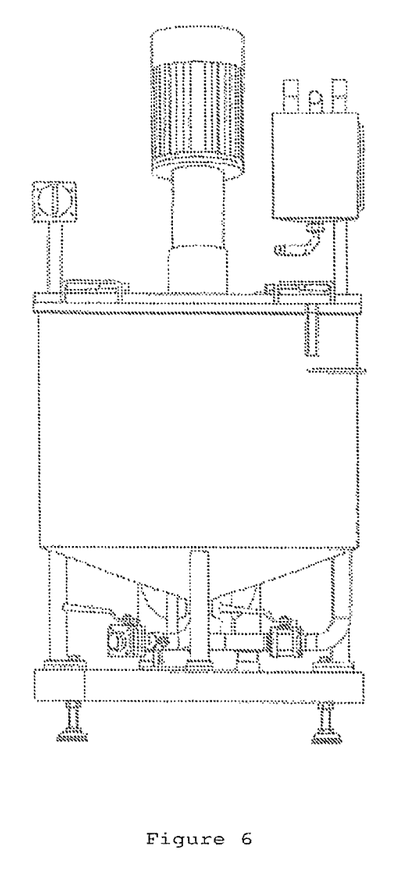
FIG. 6: shows a front view of the apparatus of FIG. 1.
Figure 7:
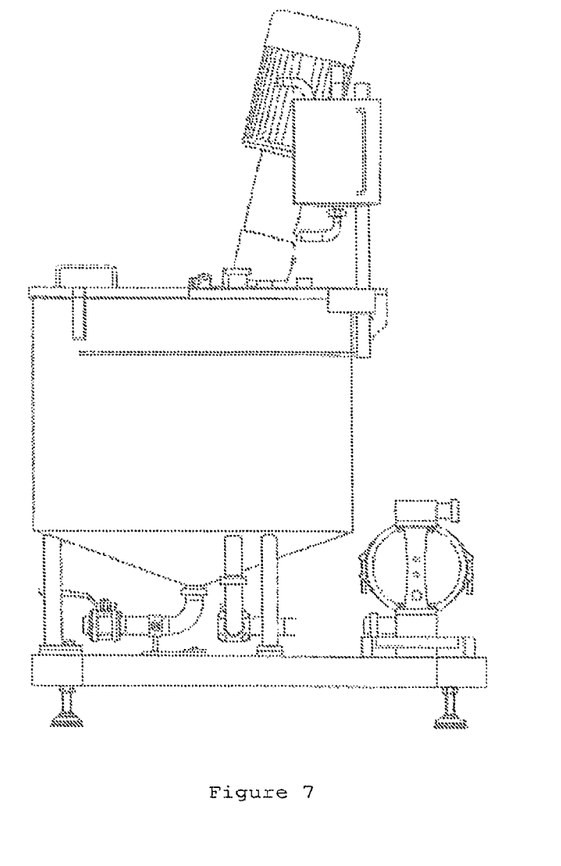
FIG. 7: shows a side view of the apparatus of FIG. 1.

FIG. 5 shows a cross section of a preferred embodiment of preservative reservoir 7 wherein the supply connection 13 on top has a curved form. In that manner, the supply of preservative agent from a supply tank (not shown) through the curved tube is directed to the inner wall of the preservative reservoir so to ensure that the maximum level sensor is not sprayed with preservative agent before the maximum level of preservative agent in the reservoir is reached and the control unit stops the supply too early.

Figure 2:
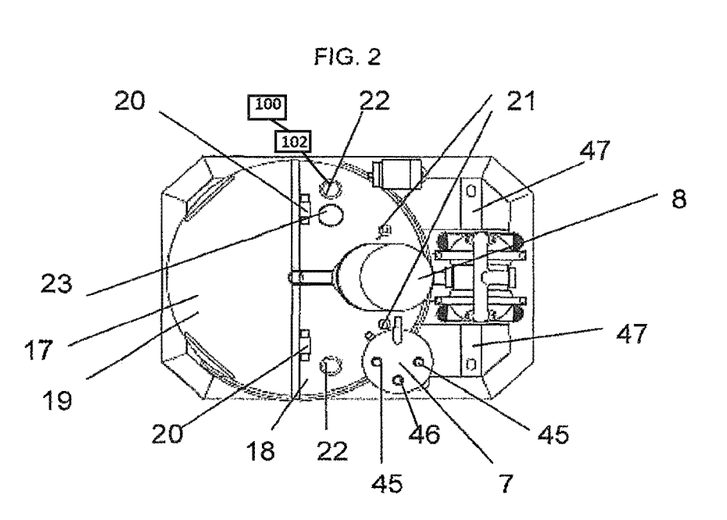
FIG. 2: shows a plan view of the apparatus of FIG. 1.

The collection tank 3 is closed off by a lid 17 having a permanently closed section 18 and a hingeable lid section 19 that is connected to the permanently closed lid section 18 by two hinges 20. The closed lid section 18 is provided with two inlet openings 21 for the inlet of preservative agent: one at both sides of the agitator 8 (see FIG. 2). Similarly, the closed lid section 18 is also provided with inlet openings 22 for the supply of mucosa at both sides of the agitator 8. The agitator 8 passes through the closed lid section and is carried by a support arm attached to the collection tank 3 (not shown). The closed lid section 18 is also provided with a sensor 23 to determine when the collected mucosa compound reaches a certain maximum level. In FIG. 1, the part of the sensor 23 extending into the collection tank 3 is indicated with interrupted lines.

The hingeable lid section 19 comprises two hand grips 24.

The bottom of the collection tank tapers down to the lower second discharge opening under an angle of 20 degrees.

Before collection of mucosa compound into the collection tank 3, the required amount of preservative agent is added and the agitator 8 is activated to stir and homogenize the mixture. After the sensor 23 detects that the maximum mucosa level is reached, a programmable control unit (not shown) stops the supply of mucosa compound to the collection tank 3. Subsequently, the control unit opens the discharge 5 and activates the pump unit 9 and preserved mucosa compound is discharged to a storage tank (not shown). After a calculated amount of time, to ensure that the minimum level in the collection tank 3 is reached, the control unit deactivates the pump unit 9. The control unit restarts the supply of preservative agent and subsequently the supply of mucosa compound into the collection tank 3 until the maximum level is reached again.

The content of the preservative reservoir 7 corresponds to the volume of preservative agent needed to preserve a mucosa volume corresponding to the volume between the maximum and minimum levels in the collection tank 3.

The lower second discharge opening 6 is connected to a hose tube 25 with a shut-off valve 26. The hose tube 25 is supported by a piping clip 27 on a rotatable arm 28 having its axis of rotation 29 in line with the second discharge opening 6.

The agitator 8 comprises a stirring rod 30 with blades 31 extending into the collection tank 3 and a drive unit 32 on top of the closed lid section 18. The agitator 8 has its longitudinal axis under an angle of about 15 degrees with the vertical. The lower end 33 of the agitator 8 is near the centre line of the collection tank 3, between the level of the first discharge opening 5 and the second discharge opening 6. The drive unit 32 of the agitator 8 is positioned near the periphery of the collection tank 3 and easily accessible for the user 2.

Figure 4:
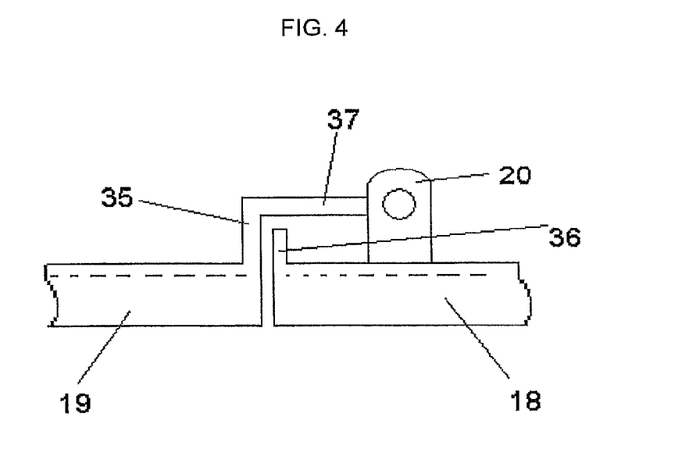
FIG. 4: shows in detail the adjacent edges of the lid sections of the apparatus of FIG. 1.

The hingeable lid section 19 is provided with a folded edge 34 covering the upper edge of the collection tank when the lid section 19 is in the closed position. Furthermore, as shown in more detail in FIG. 4, the adjacent edges of the hingeable lid section 19 and the permanently closed lid section 18 are provided with raised edges 35, 36. The raised edge 35 of the hingeable lid section 19 has a folded tip 37 extending over the raised edge 36 of the permanently closed section. The folded tip edge 37 is connected to the hinges 20.

For safety reasons, a sensor 38 is arranged on the outer wall of the collection tank 3, just below the hingeable lid 19 to send a stop signal to a control unit (not shown) for stopping the agitator 8 when the hingeable lid section 19 is not in its closed position.

The support pallet 10 is shown separately in FIG. 3. The pallet 10 comprises a rectangular frame of a corrosion resistant steel with one traverse cross beam 39, a central longitudinal cross beam 40 at one side of the traverse cross beam 39 and two longitudinal cross beams 41 at the other side of the traverse cross beam 39. In a preferred embodiment the support pallet 10 comprises two traverse cross beams 47, between longitudinal cross beams 41 and the outer frame. The two traverse cross beams 47 provide support for a, e.g. U shaped, bar upon which a local control unit can be mounted.

The dimensions of the pallet 10 are such that, in plan view, none of the other components of the apparatus 1 extends past the outline of the pallet 10.

The collection tank 3 rests on three legs 42 bolted to the frame 10. The frame 10 itself stands on height adjustable supports (43; see FIG. 1).

A guiding bar 44 or rod for attachment of electric cables extends horizontally over part of the outer wall of the collection tank 3.

Figure 8:
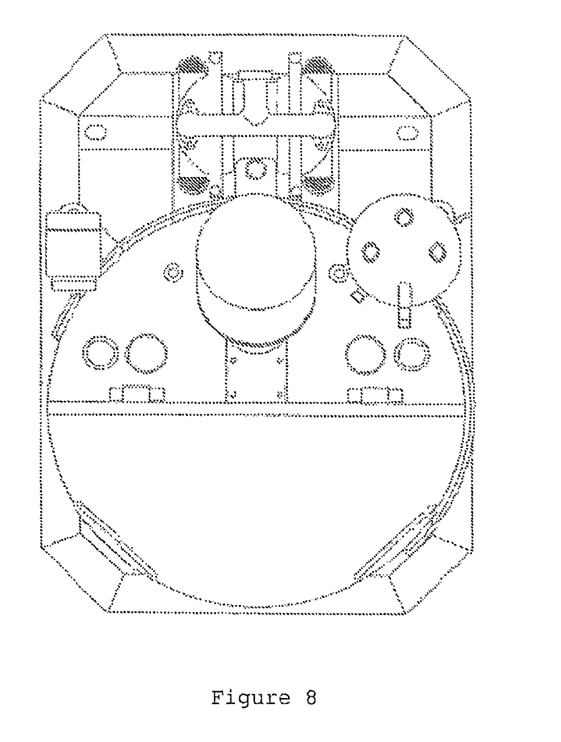
FIG. 8: shows a plan view of the apparatus of FIG. 1.
Figure 9:
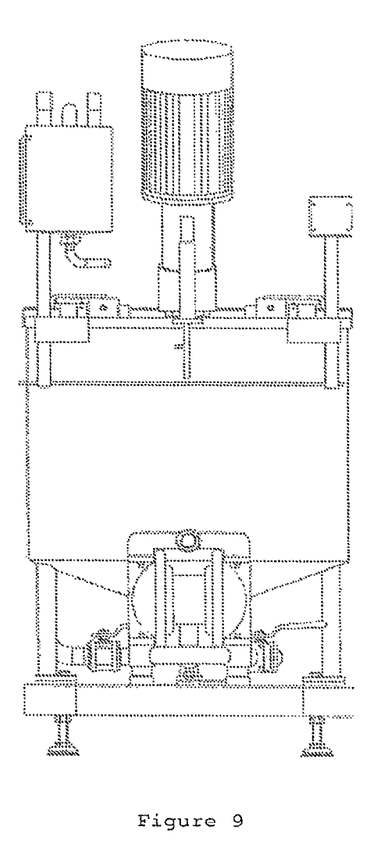
FIG. 9: shows a back view of the apparatus of FIG. 1.
Figure 10:
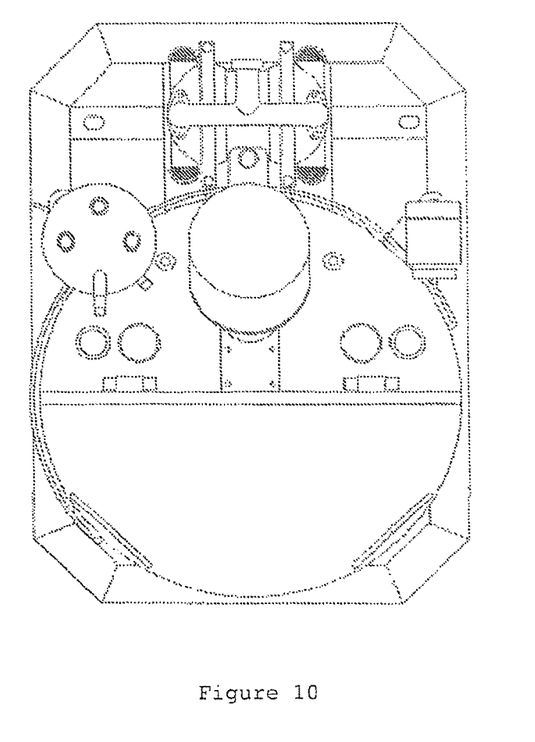
FIG. 10: shows a plan view of an apparatus according to the present invention.

FIGS. 8 and 10 show filling orifices 22 provided at both sides of the drive unit of the agitator as well as sensors 23 for detecting the maximum level of mucosa compound in the collection tank. FIG. 10 differs from FIG. 8 in that the preservative reservoir 7 has been positioned at the other side of the agitator 8.

The invention claimed is:

1. A method for preserving slaughter offal comprising the following steps:
   a) providing an empty preservative reservoir and an empty collection tank, each with a minimum height level sensor placed at a minimum height and a maximum height level sensor placed at a maximum height,
   b) filling the preservative reservoir with a preservative agent from an automatic supply of preservative agent,
   c) using a programmable control unit to stop the automatic supply of preservative agent adding preservative agent after the maximum height level sensor in the preservative reservoir detects that a maximum height level is reached,
   d) adding the preservative agent in the preservative reservoir to the collection tank until the minimum height level sensor in the preservative reservoir indicates the minimum height level is reached,
   e) filling the collection tank (3) with mucosa from an automatic supply of mucosa,
   f) using the programmable control unit to stop the automatic supply of mucosa adding the mucosa after the maximum height level sensor in the collection tank detects that a maximum height level is reached, wherein the mucosa and the preservative agent are mixed to form a preserved mucosa compound,
   g) opening a closable discharge and activating a pump unit and discharging the preserved mucosa compound in the collection tank to a container or storage tank, and
   h) closing off the discharge and deactivating the pump unit when the preserved mucosa compound in the collection tank reaches a minimum level detected by the minimum height level sensor.

2. The method of claim 1, wherein steps b)-h) are repeated.

* * * * *

UNITED STATES PATENT AND TRADEMARK OFFICE
CERTIFICATE OF CORRECTION

| | | |
|---|---|---|
| PATENT NO. | : 11,051,508 B2 | |
| APPLICATION NO. | : 16/381348 | |
| DATED | : July 6, 2021 | |
| INVENTOR(S) | : Gijtenbeek et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 141 days.

Signed and Sealed this
Fourteenth Day of February, 2023

Katherine Kelly Vidal
*Director of the United States Patent and Trademark Office*